Dec. 27, 1966 G. L. THOMAS, JR Plant Pat. 2,698
WATER LILY PLANT
Filed Oct. 14, 1965
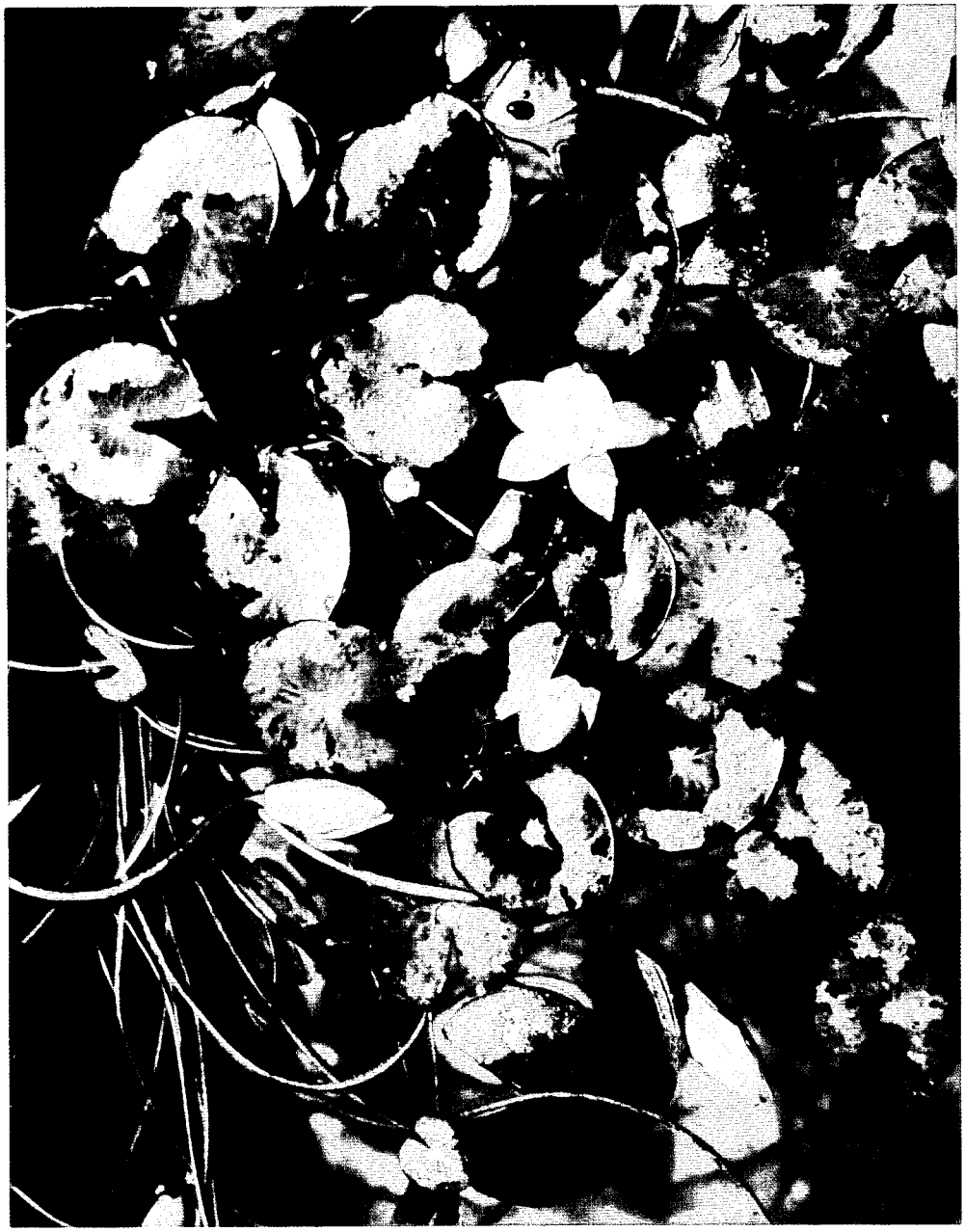
Inventor.
George L. Thomas, Jr.
By: Robb & Robb
Attorneys.

United States Patent Office

Plant Pat. 2,698
Patented Dec. 27, 1966

2,698
WATER LILY PLANT
George L. Thomas, Jr., Lilypons, Md. 52560
Filed Oct. 14, 1965, Ser. No. 496,208
1 Claim. (Cl. Plt.—68)

The present invention relates to a new and distinct variety of water lily plant which was originated by me by crossing the variety known as "Chromatella" (unpatented) with the variety known as "Tetragona" (unpatented), the former being the pollen parent and the latter being the seed parent.

The primary objective of this breeding was to produce a new and improved miniature water lily variety which will readily thrive when grown in an indoor aquarium under artificial light or under direct sunlight. This objective was fully achieved, along with other desirable improvements, as evidenced by the following unique combination of characteristics which are outstanding in my new water lily variety, and which distinguish it from its parents, as well as from all other varieties of which I am aware:

(1) Miniature plant and flower size;
(2) Good hardiness; and
(3) The ability of readily thrive when grown in indoor aquariums as well as outdoors.

In comparison with its seed parent, "Tetragona," the new variety produces yellow flowers, whereas the flowers of this parent are white.

As compared with its pollen parent, "Chromatella," the new variety is distinctly smaller in all respects and is the only known hardy water lily that is capable of being grown under artificial light.

A sexual reproduction of my new variety by root division, as performed by me at Lilypons, Maryland, shows that the foregoing characteristics and distinctions are established and come true through succeeding propagations.

The accompanying drawing shows typical specimens of the vegetative growth and flowers of my new variety in different stages of development and as depicted in color as nearly true as it is reasonably possible to make the same in an illustration of this character.

The following is a detailed description of my new water lily variety, as based upon observations of specimens grown at Lilypons, Maryland, with color terminology in accordance with the Nickerson Color Fan, published by Munsell Color Company, Inc., of Baltimore, Maryland:

Breeding: Seedling.
*Seed parent.*—"Tetragona."
*Pollen parent.*—"Chromatella."
Propagation: Holds its distinguishing characteristics through succeeding propagations by root division.

*Plant*

Foliage:
*Submerged leaves.* — Shape — arrowhead. Length (from petiole to sinus)—1¼ inches. Color: Upper side—Moderate Yellow-Green, Plate 2.5GY 5/5, with flecks of Moderate Reddish-Brown, Plate 7.5R 3/6; Under side—Dark Greenish-Yellow, Plate 10Y 6/7 on main leaves.
*Main floating leaves.* — Shape — basically oval. Length (from petiole to sinus)—1¾ inches. Color: Upper side—Moderate Olive Green, Plate 7.5GY 4/4, with flecks of Dark Red, Plate 2.5R 3/7; Under side—Light Olive, Plate 5.7Y 5/5, with flecks of Dark Red, Plate 2.5R 3/7.
*Mature leaves.*—Shape—basically round. Size—2½ inches. Color: — Upper side — Moderate Olive Green, Plate 7.5GY 4/4, with flecks of Grayish-Olive Green, Plate 7.5GY 3/2; Underside—Light Olive, Plate 5.7Y 5/5, with flecks of Dark Red, Plate 2.5R 3/7. Left stem: Color—Moderate Yellow-Green, Plate 2.5GY 5/5. Length—Varies according to water depth.

*Flower*

Bloom:
*Habit.*—Continuous.
*Size.*—About 3 inches if flower is spread manually to maximum diameter.
*Color.*—Brilliant Greenish-Yellow, Plate 7.5Y 9/8; softer and lighter than color of other hardy Yellow water lilies.
*Number of days open.*—4 or 5.
*Fragrance.*—Slight. Nature—sweet.
*Number open at one time.*—1 or 2 per crown, but plant develops multiple crown so that in 2 years of development, the plant will have at least 6 flowers open at a time.
*Distance standing out of water.*—Flowers float on water surface.

Buds:
*Shape.*—Cupped; normal water lily shape.
*Color.*—Dark Greenish-Yellow, Plate 10Y 6/7.

Scape:
*Color.*—Strong Yellow-Green, Plate 5GY 6/8.
*Height above water.*—¼ inch.
*Ridges.*—Not apparent.

Sepals:
*Number.*—4.
*Color.*—Moderate Yellow-Green, Plate 2.5GY 5/5.
*Length.*—1½ inches.
*Width.*—½ inch.
*Shape*—Cupped; characteristic water lily shape.
*Texture.*—Similar to that of both parent varieties.

Petals:
*Number.*—16.
*Shape.*—Slightly curved, with moderately rounded tips in characteristic fashion of cup-shaped water lilies.
*Length.*—Outer petals—1½ inches. Inner petals—¾ inch.
*Width.*—Outer petals—½ inch. Inner petals—⅜ inch.
*Color.*—Brilliant Greenish-Yellow, Plate 7.5Y 9/8.

Stamens:
*Number.*—50.
*Length.*—Outer—⅝ inch. Inner—5/16 inch.
*Appendages.*—With.
*Shape.*—Characteristic shape for cup-shaped water lilies.

Carpels:
*Number.*—7.
*Color.*—Vivid Greenish-Yellow, Plate 7.5Y 8/12.
*Length.*—⅛ inch.

Stigma: Color—Vivid Grenish-Yellow, Plate 7.5Y 8/12.
Receptive: Yes.

*Fruit*

Shape: Spherical.

Size:

*Length.*—7/16 inch.

*Width (at widest bulge).*—5/16 inch.

Seeds: Present.

Fertile: Yes.

Shipping Quality: Excellent.

Lasting Quality: Excellent.

I claim:

A new and distinct variety of water lily plant, substantially as herein shown and described, characterized particularly as to novelty by the unique combination of a miniature plant and flower size, good hardiness, and the ability to readily thrive when grown in indoor aquariums under either artificial or natural light, as well as outdoors.

No references cited.

ABRAHAM G. STONE, *Primary Examiner.*

R. E. BAGWILL, *Assistant Examiner.*